United States Patent [19]

Baba et al.

[11] Patent Number: 4,462,962
[45] Date of Patent: Jul. 31, 1984

[54] LIQUID CHROMATOGRAPHIC FLOW CELL

[75] Inventors: Nobuyuki Baba, Atsugi; Keiichi Housako, Sagamihara, both of Japan

[73] Assignee: Toyo Soda Manufacturing Co., Ltd., Shinnanyo, Japan

[21] Appl. No.: 512,678

[22] Filed: Jul. 11, 1983

[30] Foreign Application Priority Data

Jul. 19, 1982 [JP] Japan .......................... 57-108186[U]

[51] Int. Cl.$^3$ ............................................ B01D 15/08
[52] U.S. Cl. .................................. 422/58; 210/198.2; 422/70
[58] Field of Search ................. 210/198.2; 422/55, 56, 422/58, 70, 91, 98; 73/61.1 C

[56] References Cited

U.S. PATENT DOCUMENTS

| | | | |
|---|---|---|---|
| 3,010,798 | 11/1961 | Whitehead et al. | 422/70 |
| 3,236,602 | 2/1966 | Isaeeli | 422/58 |
| 4,019,372 | 4/1977 | Paakell | 210/198.2 |
| 4,361,540 | 11/1982 | Weinberg | 422/98 |
| 4,400,353 | 8/1983 | Meseroe | 422/58 |

OTHER PUBLICATIONS

High Performance Liquid Chromatography by Knox. Edinburgh University Press, Edinburgh, Scotland, Chapter 10-Detector and Reactor Systems, 1980.
"A Conductimetric Detector with a Wide Dynamic Range for Liquid Chromatography", by Vratislav Svoboda and Jaroslav Marsal-Journal of Chromatography, 148, (1978), 111-116.
"The Photo-Conductivity Detector-A New Selective Detector for HPLC", by D. J. Popovich, J. B. Dixon, and B. J. Ehrlich, Journal of Chromatographic Science, vol. 17, Dec. 1979, pp. 643-650.
"A Sensitive Low Volume Conductivity Detector for Liquid Chromatography", by Robert L. Pecsok and Dennis L. Saunders, Analytical Chemistry, vol. 40, No. 11, Sep. 1968, pp. 1756-1757.

Primary Examiner—John Adee
Attorney, Agent, or Firm—Stevens, Davis, Miller & Mosher

[57] ABSTRACT

A liquid chromatographic flow cell for measuring constituents of a specimen solution, comprising at least two electrodes, each having a first through hole, an insulating member having a second through hole and so disposed as to electrically insulate the electrodes from each other, a first and a second supporting members for clamping therebetween the electrodes and the insulating member in such a way that the first and the second through holes are coaxially aligned so as to define a first passage of the specimen solution and having, respectively, a second passage and a third passage of the specimen solution which communicate with the first passage, a first light guiding member for guiding a light for measuring an absorbance of the specimen solution into the second passage defined in the first supporting member, and a second light guiding member for guiding the light transmitted through the third passage defined in the second supporting member to means for measuring an absorbance of the specimen solution. Both the electric conductivity and absorbance of the constituents of a specimen solution dissolved from a column can be measured simultaneously and continuously within the same cell.

7 Claims, 10 Drawing Figures

LIQUID CHROMATOGRAPHIC FLOW CELL

BACKGROUND OF THE INVENTION

1. Field of the Invention

The present invention relates to a flow cell for liquid chromatography of the type in which both the electric conductivity and absorbance of the constituents of a specimen solution dissolved from a column can be measured simultaneously and continuously within the same cell, and more particularly to a flow cell for liquid chromatography which is adapted to measure both the variations with respect to time in electric conductivity and absorbance of a solution flowing at a very low flow rate within the same cell.

2. Description of the Prior Art

Variations in electric conductivity of a solution are one of the factors which exhibit the fundamental properties of an electrolyte and the quantity of the electrolyte can be measured by measuring the electric conductivity of the solution. Furthermore, the variations in volume of a specimen can be measured by measuring the difference in electric conductivities between the solution and specimens contained in the solution.

Furthermore, the properties and the variations in quantity of the constituents of a specimen can be measured by the chemical reactions of particular constituents of the specimen with a light of a predetermined wavelength and by measuring the absorbance of the solution.

These analyzing methods are, for instance, disclosed in the following literatures:

"A Sensitive Low Volume Conductivity Detector for Liquid Chromatography" Robert L. Pecsok et al., ANALYTICAL CHEMISTRY, Vol. 40, No. 11, 1968, Sept., P. 1756-1757;

"A CONDUCTIMETRIC DETECTOR WITH A WIDE DYNAMIC RANGE FOR LIQUID CHROMATOGRAPHY" Vratislav Svoboda et al., Journal of Chromatography, 148(1978), pp. 111-116 and 148(1978), pp. 111-116; and "The Photo-Conductivity Detector—A New Selective Detector for HPLC" D. J. Popovich et al., Journal of Chromatographic Science, Vol. 17, 1979, Dec. pp. 643-650.

The devices for measuring the electric conductivity and the devices for measuring the absorbance based on the above-described literatures are separately marketed and used.

With increased uses of chromatography, various specimens are used and complicated specimens containing unknown constituents are increased, so that both a detecting device for measuring the electric conductivity and a detecting device for measuring the absorbance must be used simultaneously. In general, these devices are connected in series, so that a solution from a column first flows through a flow cell of the detecting device for measuring the electric conductivity and then flows through a flow cell of the detecting device for measuring the absorbance. The series-connected chromatographic process has the following serious disadvantages.

First, a solution flowing through a first flow cell causes turbulence, which produces further turbulence at the connection between the first and second flow cells. As a result, a chromatogram of specimen constituents dissolved from the column is distorted. The tubulence especially disturbs the measurement by the detecting device for measuring the absorbance. Especially in liquid chromatography, the quantity of a separated constituent of the specimen is determined by measuring the height or area of a peak of a chromatogram and the properties of the constituent are analyzed in response to a time required for dissolving the constituent. It follows, therefore, that the distortions of the peaks due to the distortion of the chromatogram cause great errors in measurement.

Secondly, conventional detecting devices for measuring the electric conductivity and absorbance have poor pressure resistance. Therefore, when use is made of a series connection of a detecting device for measuring the electric conductivity and a detecting device for measuring the absorbance, it is often likely that a solution leaks and that a detecting cell is broken. As a result, they unfit for use.

In order to solve the above described disadvantages there has been employed a method in which a solution derived from a column is divided by a divider or the like into two detectors. According to this method, the diffusion of the constituents of a specimen can be reduced, but turbulence occurs in the divider or the like so that the latter is clogged with dust entrained in the solution. Furthermore, a ratio of such a division varies due to a temperature variation, and accordingly the measurements with a good reproducibility are difficult.

SUMMARY OF THE INVENTION

A primary object of the present invention is, therefore, to provide a flow cell for chromatography which can substantially overcome the above and other serious disadvantages and problems encountered in the case that a detecting device for measuring an electric conductivity and a detecting device for measuring an absorbance are simultaneously used so that both the variations in electric conductivity and variations in absorbance can be simultaneously and continuously measured within the same flow cell.

In order to achieve the above-described object, in a flow cell for use in chromatography of the type in which the constituents or components of a specimen solution obtained from a column are measured a liquid chromatographic flow cell according to the present invention comprises at least two electrode each having a first through hole, an insulating member having a second through hole and for electrically insulating the two or more electrodes from each other, a first and a second supporting members for clamping therebetween the electrodes and the insulating means in such a way that the first and the second through holes are coaxially aligned so as to define a first passage through which the specimen solution flows, and further having a second passage and a third passage which communicate, respectively, with the first passage, a first guiding member for guiding a light for measuring an absorbance of the specimen solution into the second passage defined in the first supporting members, and a second guiding member for guiding the light transmitted through the third passage defined in the second supporting member to means for measuring the absorbance of the specimen solution.

In a first preferred embodiment of a liquid chromatographic flow cell according to the present invention, the insulating member comprises a hollow tube having the second through hole. The electrodes and the first and second supporting members are in the form of metal blocks disposed at the respective ends of the hollow tube. The metal blocks define the first through holes of the electrodes and the first passages of the first and second supporting members which communicate with the first through holes, respectively. A first and a second optically transparent members are disposed on the respective outer sides of the first and second supporting members so as to define the second passages with the first and second supporting members. The first and second optically transparent members forms the first and second light guiding members, respectively.

In a second preferred embodiment of a liquid chromatographic flow cell according to the present invention, each of the electrodes has metal plates, each having a through hole. The insulating member has insulating plates, each having a through hole. The metal plates and the insulating plates are alternately laminated, in a manner that the first and second through holes are coaxially aligned with each other. The first and second supporting members are disposed at the respective ends of the laminated assembly of the metal plates and the insulating plates.

Here, it is preferable that the first supporting member is formed with a first recess which opens at the bottom thereof to one end of the first passage, and the second supporting member is formed with a second recess which opens at the bottom thereof to the other end of the first passage. The first and second light guiding members comprise a first and a second optical transparent plates, respectively, which are fitted into the first and second recesses so as to define the second and third passages, respectively.

Here, an optical filter to which the light for measuring the absorbance is incident may be disposed in the first recess, and the optical detector for measuring the absorbance may be disposed in the second recess.

In a third preferred embodiment of a liquid chromatographic flow cell according to the present invention, the electrodes have two metal plates. The insulating member has a plurality of hollow rods made of insulating material, one of which is interposed between the two metal plates, and the remaining hollow rods of which are disposed at the outer ends, respectively, of the two metal plates, in a manner that a hollow tube having the first and second through holes in common is formed. The first and second supporting members are disposed at the ends, respectively, of the hollow tube. The first and second light guiding members have a first and a second optically transparent members which are disposed adjacent to the first and second supporting members, respectively, to define the second and third passages with the first and second supporting members.

In a fourth preferred embodiment of a liquid chromatographic flow cell according to the present invention, the electrodes are formed by a first pair of walls which are in opposite to each other, the insulating members are formed by a second pair of walls which are in opposite to each other and are interposed between the first pair of walls as the electrodes so as to define a hollow tube with a rectangular cross sectional configuration. The first and second supporting members are disposed at the respective ends, of the hollow tube. The first and second light guiding members have a first and a second optically transparent disposed adjacent to the first and second supporting members, so as to define the second and third passages, respectively.

The above and other objects, effects and advantages of the present invention will become more apparent from the following description of preferred embodiments thereof taken in conjunction with the accompanying drawings.

DETAILED DESCRIPTION OF THE PREFERRED EMBODIMENTS

Same reference numerals are used to designate similar parts throughout the figures.

Figures 1A, 1B:
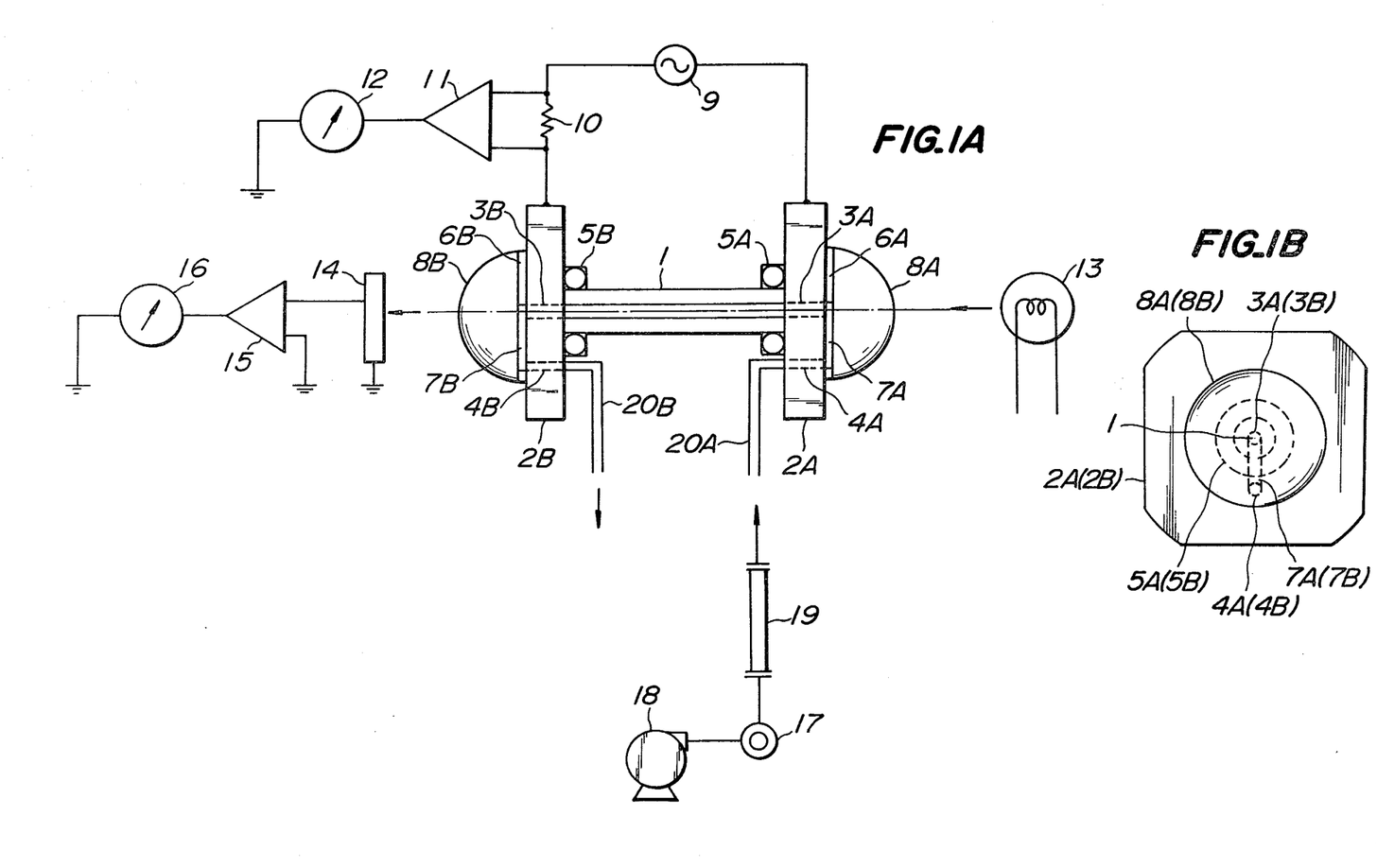
FIG. 1A is a front view showing a first embodiment of a flow cell according to the present invention, of which an electric measuring circuit is shown in the form of an electrical circuit diagram.
FIG. 1B is a side view of the flow cell shown in FIG. 1A.

FIGS. 1A and 1B show a first embodiment of a flow cell according to the present invention. Reference numeral 1 designates a hollow tube having a small inner diameter and forming a part of a flow cell, and 2A and 2B, cell holders which are in the form of a metal block and are provided with through holes 3A and 3B adapted to communicate with the ends of the hollow tube 1, respectively, a specimen charging inlet 4A and a specimen discharging outlet 4B. The hollow tube 1 is clamped between the cell holders 2A and 2B in such a way that the axis of the hollow tube 1 is coaxial with the axes of the through holes 3A and 3B. The hollow tube 1 is securely held in position with O-rings 5A and 5B.

Packings 6A and 6B are abutted against the outer surfaces of the cell holders 2A and 2B, respectively, and formed with grooves or passages 7A and 7B, respectively, which intercommunicate between the through holes 3A and 3B on the one hand and the specimen inlet 4A and the specimen outlet 4B on the other hand. When the packings 6A and 6B are mounted on the cell holders 2A and 2B, respectively, the grooves or liquid passages 7A and 7B may be maintained liquid-tight. Mounted on the packings 6A and 6B are optically transparent members 8A and 8B, respectively, which absorb a little or hardly absorb a light within a light wavelength range of a light to be used. The optically transparent members 8A and 8B further serve to maintain the grooves or liquid passages 7A and 7B of the packings 6A and 6B liquid tight.

When use is made of a light source 13 (to be described in more detail hereinafter) emitting ultraviolet light rays, the optically transparent members 8A and 8B may be made of silica glass in the form of a dome or hemisphere, as illustrated in FIG. 1A. Alternatively, if the light source 13 emits visible light rays, the optically transparent members 8A and 8B may be made of silica glass or pyrex glass or acrylic resin in the form of a dome or hemisphere. It is preferable that the transparent members 8A and 8B have a hemispherical form so as to serve as a lens for converging light rays.

The hollow tube 1 is used as a measuring cell, so that the cell holders 2A and 2B serve as electrodes for measuring the electric conductivity of a liquid or solution flowing through the hollow tube 1. On the other hand, the combination of the hollow tube 1, the through holes 3A and 3B of the cell holders 2A and 2B and the packings 6A and 6B are used as a measuring cell or form an optical path for measuring an absorbance. In this way, the flow cell of the liquid chromatography according to the present invention is constructed.

An AC current having a predetermined sinusoidal waveform is applied to the cell holders 2A and 2B, which function as electrodes, through a range resistor 10 from a AC power supply 9 which may be for instance an oscillator for generating a sinusoidal current at the frequency of 1 KHz so that a variation in electrical resistance of a liquid flowing through the hollow tube 1 from the electrode 2A to the electrode 2B is measured in terms of a variation in voltage across the range resistor 10. The detected voltage across the range resistor 10 is applied to an amplifier 11, the output of which in turn is applied to a voltmeter 12, so that an electric conductivity of the specimen or liquid flowing through the tube 1 can be obtained in terms of voltage.

The light source 13, which may be a tungsten lamp or mercury lamp, is disposed in front of the optically transparent member 8A, so that a light emitted from the light source 13 impinges the optically transparent member 8A. The incident light is transmitted through the through hole 3A, the hollow tube 1 and the through hole 3B of the block 2B. Then, the light is guided to the optically transparent member 8B. The light emitted from the member 8B impinges a photo detector 14 such as a silicon photo cell or a cadmium sulfide element coated with fluorescent material. The output from the photo detector 14 is applied to an amplifier 15, where the detection output is subject to a logarithmic conversion. The output from the amplifier 15 in turn is applied to a voltmeter 16, so that an absorbance of the liquid flowing through the flow cell can be obtained in terms of voltage.

A specimen solution is charged through a specimen inlet 17 and forced into a separation column 19 by a pump 18 and a dissolved specimen liquid is introduced through a pipe 20A into the inlet 4A. Therefore, the specimen liquid is guided through the groove or passage 7A and the through hole 3A to the hollow tube 1. Then, the specimen liquid from the hollow tube 1 flows into the through hole 3B and the groove or passage 7B and finally is discharged from the outlet 4B into a pipe 20B.

According to the present invention, not only the problems encountered in the prior art chromatography can be substantially overcome, but also the diffusion of the constituents of the specimen solution due to the turbulent flow through the cell can be avoided. Furthermore, the flow cell can be made compact in size, so that it can be incorporated in a thermostatic chamber to remove a variation in electric conductivity due to a temperature variation.

Figures 2A, 2B:
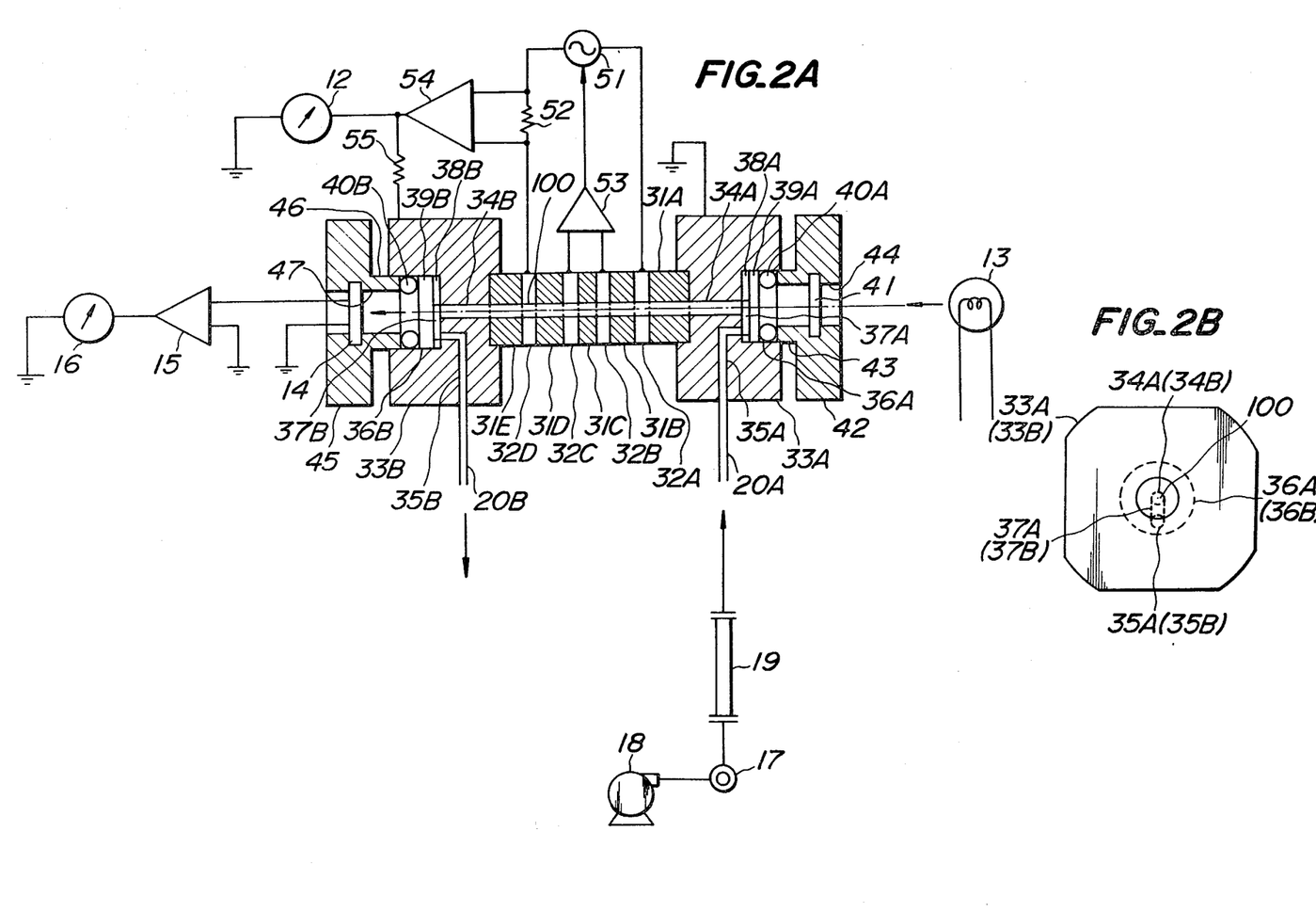
FIG. 2A is a sectional view showing a second embodiment of a flow cell according to the present invention, of which an electric measuring circuit is shown in the form of an electrical circuit diagram.
FIG. 2B is a side view of the flow cell shown in FIG. 2A.

FIGS. 2A and 2B show a second embodiment of a flow cell according to the present invention. Insulating plates 31A, 31B, 31C, 31D and 31E, each having a center through hole, and metal plates 32A, 32B, 32C and 32D, each having a center through hole, are alternately laminated or sandwiched so that a specimen liquid passage 100 is defined. The insulating plates 31A–31E and the metal plates 32A–32D are securely and liquid-tightly maintained by clamping, with fixing screws, cell holders 33A and 33B which are attached to the insulating plates 31A and 31E, respectively, in a manner that the through holes of the insulating plates 31A–31E and the metal plates 32A–32D are coaxial. The cell holders 33A and 33B may be in the form of a metal block. That is, the cell holder 33A has a through hole 34A which is in coaxial relationship with the through hole of the insulating plate 31A or the specimen passage 100, while the cell holder 33B has a through hole 34B which is in coaxial relationship with the through hole of the insulating plate 31E or the specimen passage 100. The cell holders 33A and 33B also have a specimen inlet 35A and a specimen outlet 45B, respectively.

In this manner, the insulating plates 31A–31E, the metal plates 32A–32D and the cell holders 33A and 33B define the specimen passage 100 which corresponds to the combination of the hollow tube 1 and the cell holders 3A and 3B in the first embodiment as shown in FIGS. 1A and 1B.

The outer surfaces of the cell holders 33A and 33B are formed with circular recesses 36A and 36B, respectively, and the through holes 34A and 34B are opened at the bottoms of the recesses 36A and 36B, respectively. The packing 38A is formed with a groove 37A which communicates the through hole 34A with the specimen inlet 35A, while the packing 38B has a groove 37B which communicates the through hole 34B with the outlet 35B. The packings 38A and 38B are fitted, respectively, in the recesses 36A and 36B in such a way that the grooves 37A and 37B are maintained liquid tight and communicate with the through holes 34A and 34B, respectively, by optically transparent plates 39A and 39B which are abutted against the packings 38A and 38B, respectively, in a manner that the transparent plates 39A and 39B are firmly secured by O-rings 40A and 40B. The transparent plates 39A and 39B may be made of the materials used to make the optically transparent members 8A and 8B in the first embodiment as shown in FIG. 1A. That is, it is to be noted that the transparent plates 39A and 39B are made of a material which absorbs a little or hardly absorbs a light within the light wavelength range of a light emitted from the light source 13.

A filter holder 42 which holds a band-pass filter 41 is mounted to the outer side of the O-ring 40A in the recess 36A of the cell holder 33A. The band-pass filter 41 absorbs a light within a predetermined wavelength range. The filter holder 42 has a projection 43 which is snugly fitted into the recess 36A of the cell holder 33A and a through hole 44 is extended through the filter holder 42 and its projection 43. The filter 41 is disposed within the through hole 44. Therefore, the light emitted from the light source 13 is guided to the through hole 44 and then passes through the filter 41, the transparent member 39A and the through hole 34A of the cell holder 33A into the passage 100 defined insided the sandwich structure by the insulating plates 31A-31E and the metal plates 32A-32D.

A detect holder 45 with the photo detect 14 is mounted to the outer side of the O-ring 40B in the recess 40B of the cell holder 33B. The detect holder 45 has a projection 46 which is snugly fitted into the recess 36B of the cell holder 33B and a through hole 47 is extended through the detect holder 45 and its projection 46. The photo detect 14 is disposed within the through hole 47. The light transmitted through the passage 100 is guided to the photo detect 14 which converts the incident light into an electrical signal in accordance with a strength of the incident light. The output signal from the photo detect 14 is applied to the amplifier 15, where the output signal is subject to a logarithmic conversion. The output from amplifier 15 is in turn applied to the voltmeter 16 as in the case of the first embodiment.

Therefore, according to the second embodiment, an optical path for measuring an absorbance is formed by the filter 41, the transparent plate 39A, the optical and liquid passage 100 and the transparent plate 39B. On the other hand, the metal plates 32A-32D and either one or both of the cell holders 33A and 33B constitute as electrodes for measuring an electric conductivity. The specimen solution is guided to flow into the flow cell through the pipe 20A from the separation column 19, so that both the measurements of an electric conductivity and an absorbance are simultaneously carried out.

Next, the measurement of an the electric conductivity in this embodiment will be described in detail. Of the metal plates 32A-32D, the metal plates 32A and 32D are used as electrodes across which a voltage is applied and the metal plates 32B and 32C are used as measuring electrodes. For instance, a series circuit consisting of a variable AC current generator 51, which is, for instance, an oscillator generating a sinusoidal current of 1 KHz, and a range resistor 52 is connected to the electrodes 32A and 32D. The electrodes 32B and 32C are connected to the input terminals of a differential amplifier 53.

The current generator 51 is controlled by the output from the differential amplifier 53. In more detail, an amount of current supplied from the current generator 51 is so controlled that a voltage produced by an electrical resistance of a solution flowing through the flow cell between the measuring electrodes 32B and 32C is always maintained at a predetermined level. Therefore, in response to the variation in current, the voltage across the range resistor 52 varies and is applied to an amplifier 54.

The cell holder 33A is grounded, while the cell holder 33B is connected through a resistor 55 to the output terminal of the amplifier 54, so that the cell holder 33B serves as a guard electrode, whereby the output from the amplifier 54 is corrected with respect to the ground potential. The amplifier output thus corrected is applied to the voltmeter 12 which indicates an electric conductivity of the specimen solution flowing through the flow cell in terms of voltage.

In addition to the advantages attained by the first embodiment, the second embodiment shown in FIG. 2A attains the advantage that an electric conductivity is stably measured without being adversely affected by polarization, variations in resistance of electrodes, external noise and the like.

Figure 3A:
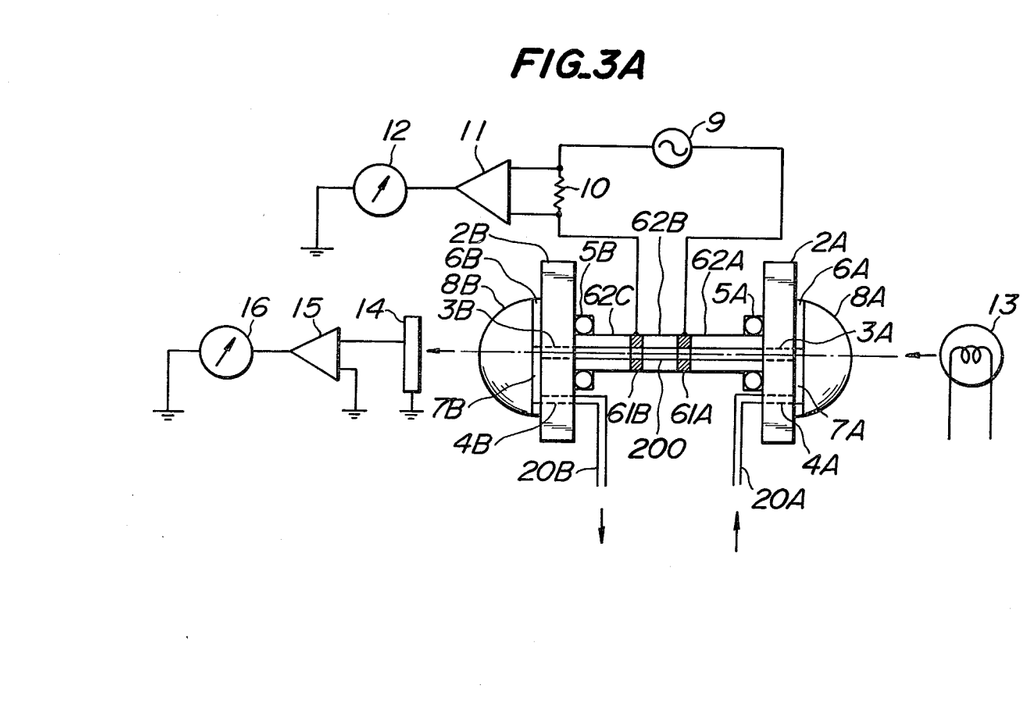
FIG. 3A is a front view showing a third embodiment of a flow cell according to the present invention, of which an electric measuring circuit is shown in the form of an electrical circuit diagram.
Figure 3B:
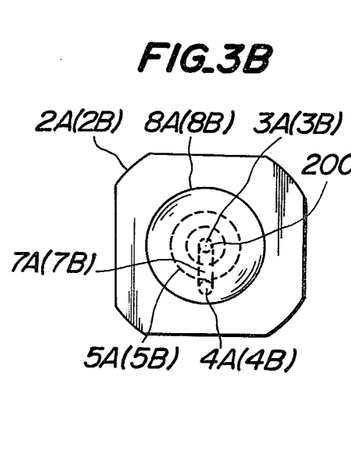
FIG. 3B is a side view of the flow cell shown in FIG. 3A.

FIGS. 3A and 3B show a third embodiment of a flow cell according to the present invention which is substantially similar in construction to the first embodiment as shown in FIGS. 1A and 1B, except that instead of the hollow tube 1, electrodes 61A and 61B, each having a center through hole are laminated alternately with insulating rods 62A, 62B and 62C, each having a center through hole. The electrode 61A is clamped between the insulating rods 62A and 62B, while the electrode 61B is clamped between the insulating rods 62B and 62C. The through holes of the electrodes 61A and 61B and the insulating rods 62A, 62B and 62C are in coaxial relationship with respect to each other, so that an optical and specimen solution passage 200 is defined. The passage 200 communicates with the inlet and outlet pipes 20A and 20B in a manner substantially similar to that described in conjunction with the first embodiment with reference to FIGS. 1A and 1B. A sinusoidal AC current is supplied from the current generator 9 through the range resistor 10 to the electrodes 61A and 61B. The mode of operation of the third embodiment is substantially similar to that of the first embodiment, so that no further explanation shall be made in this specification.

In the first and second embodiments, the hollow tube 1, the liquid passage 100 and the through holes 3A and 3B have circular cross sectional configurations, but it is to be understood that the present invention is not limited thereto. For instance, they may have square cross sectional configurations. That is, any suitable cross sectional configurations may be selected depending upon desired purposes or designs.

Figure 4A:
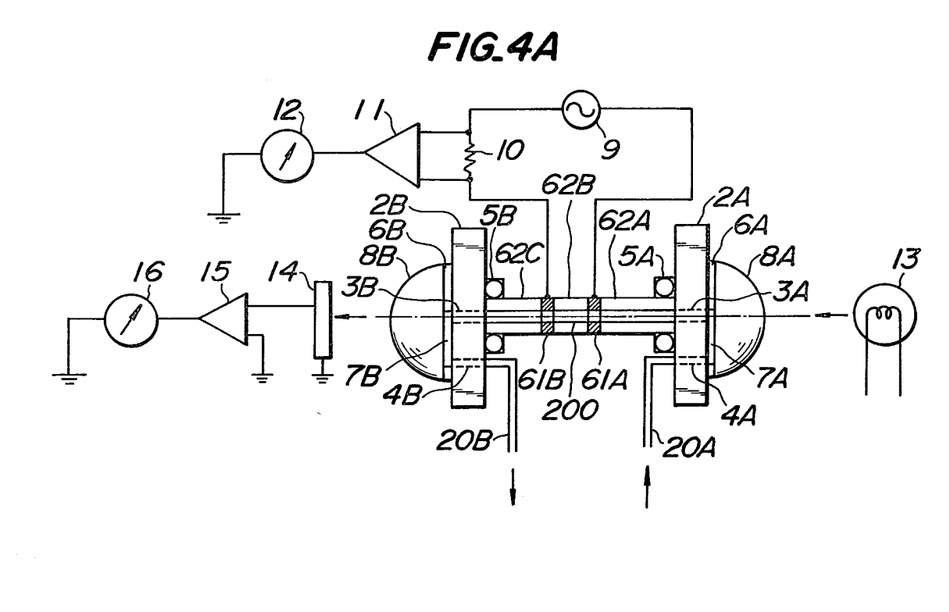
FIG. 4A is a front view showing a fourth embodiment of a flow cell according to the present invention, of which an electric measuring circuit is shown in the form of an electrical circuit diagram.
Figure 4B:
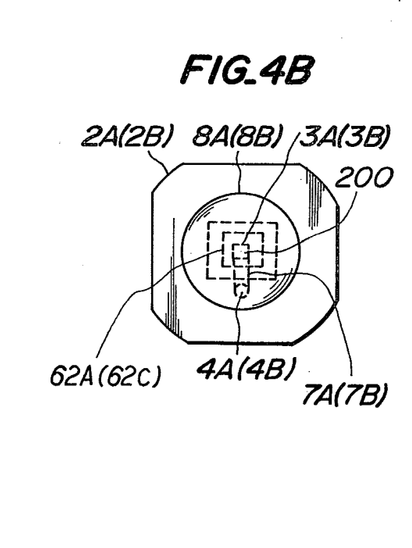
FIG. 4B is a side view of the flow cell shown in FIG. 4A.

A fourth embodiment of the present invention shown in FIGS. 4A and 4B is substantially similar to the third embodiment as shown in FIGS. 3A and 3B, except that the electrodes 61A and 61B, the insulating rods 62A-62C and the cell holders 2A and 2B have the through holes having rectangular cross sectional configurations.

Figure 5A:
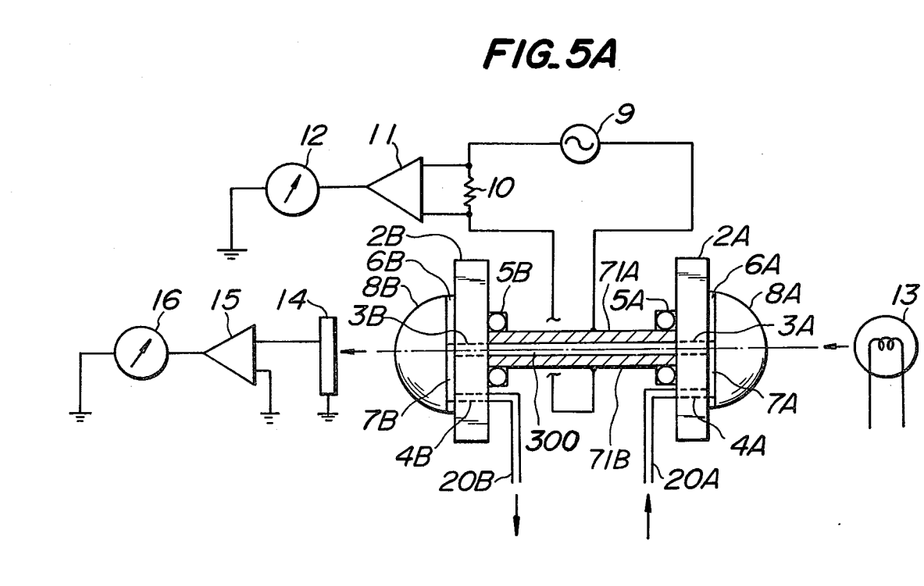
FIG. 5A is a front view of a fifth embodiment of a flow cell according to the present invention, an electric measuring circuit is shown in the form of an electrical circuit diagram.
Figure 5B:
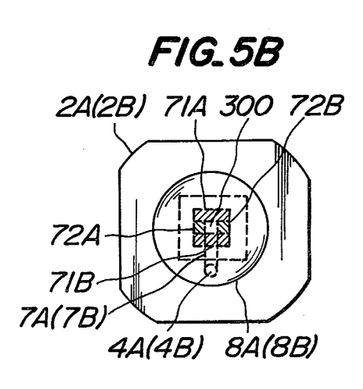
FIG. 5B is a side view of the flow cell shown in FIG. 5A.

When the optical and liquid passage has a rectangular cross sectional configuration, a pair of opposed walls of the passage may be used as electrodes for measuring an electric conductivity, while another pair of opposed walls may be used as insulating plates for insulating these electrodes, as will be described in detail with reference to a fifth embodiment of the present invention as shown in FIGS. 5A and 5B.

Referring to FIG. 5B, in the fifth embodiment, electrodes 71A and 71B are disposed in opposed relationship with each other, while insulating plates 72A and 72B are interposed between the electrodes 71A and 71B and in opposed relationship with each other, so that an optical and liquid passage 300 having a square cross sectional configuration is defined. A sinusoidal AC current is supplied from the current generator 9 through the range resistor 10 to the electrodes 71A and 71B, so that an electric conductivity of the specimen solution flowing through the flow cell is measured in a manner substantially similar to that described above. In the fifth embodiment, the cell holders 2A and 2B are made of an insulating material.

As described above, according to the present invention, variations in electric conductivity and absorbance of a specimen solution can be simultaneously and continuously measured within one and the same flow cell. Therefore, the present invention can substantially overcome the disadvantages encountered when a detecting device for measuring an electric conductivity and a detecting device for detecting a absorbance are connected in series or when a specimen flowing out of a column is divided by a dividing means into a detecting device for measuring an electric conductivity and a detecting device for measuring the an absorbance. Thus, errors in such measurements can be reduced to a minimum. Liquid leakage and damage to a detection cell can be avoided. In addition, an electrical conductivity and an absorbance are measured with a good reproducibility.

What is claimed is:

1. A liquid chromatographic flow cell for measuring constituents of a specimen solution, comprising:
   (a) at least two electrodes, each having a first through hole;
   (b) an insulating member having a second through hole and so disposed as to electrically insulate said at least two electrodes from each other;
   (c) a first and a second supporting members for clamping therebetween said at least two electrodes and said insulating member in such a way that said first through holes and said second through holes are coaxially aligned so as to define a first passage of said specimen solution and having, respectively, a second passage and a third passage of said specimen solution which communicate with said first passage;
   (d) a first light guiding member for guiding a light for measuring an absorbance of said specimen solution into said second passage defined in said first supporting member; and
   (e) a second light guiding member for guiding the light transmitted through said third passage defined in said second supporting member to means for measuring an absorbance of said specimen solution.

2. A liquid chromatographic flow cell as claimed in claim 1, wherein said insulating member comprises a hollow tube having said second through hole;
   said electrodes and said first and second supporting members are in the form of metal blocks disposed at the respective ends of said hollow tube;
   said metal blocks define said first through holes of said electrodes and said first passages of said first and second supporting members which communicate with said first through holes, respectively; and
   a first and a second optically transparent members are disposed on the respective outer sides of said first and second supporting members so as to define said second passages with said first and second supporting members, said first and second optically transparent members forming said first and second light guiding members, respectively.

3. A liquid chromatographic flow cell as claimed in claim 1, wherein each of said electrodes has metal plates each having a through hole;
   said insulating member has insulating plates, each having a through hole;
   said metal plates and said insulating plates are alternately laminated, in a manner that said first and second through holes are coaxially aligned with each other; and
   said first and second supporting members are disposed at the respective ends of the laminated assembly of said metal plates and said insulating plates.

4. A liquid chromatographic flow cell as claimed in claim 3, wherein said first supporting member is formed with a first recess which opens at the bottom thereof to one end of said first passage;
   said second supporting member is formed with a second recess which opens at the bottom thereof to the other end of said first passage; and
   said first and second light guiding members comprise a first and a second optical transparent plates, respectively, which are fitted into said first and second recesses so as to define said second and third passages, respectively.

5. A liquid chromatographic flow cell as claimed in claim 4, wherein an optical filter to which said light for measuring the absorbance is incident is disposed in said first recess, and said optical detector for measuring the absorbance is disposed in said second recess.

6. A liquid chromatographic flow cell as claimed in claim 1, wherein said electrodes have two metal plates;
   said insulating member has a plurality of hollow rods of insulating material, one of which is interposed between said two metal plates, and the remaining hollow rods of which are disposed at the outer ends, respectively, of said two metal plates, in a manner that a hollow tube having said first and second through holes in common is formed;
   said first and second supporting members are disposed at the ends, respectively, of said hollow tube; and
   said first and second light guiding members have a first and a second optically transparent members which are disposed adjacent to said first and second supporting members, respectively, to define said second and third passages with said first and second supporting members.

7. A liquid chromatographic flow cell as claimed in claim 1, wherein said electrodes are formed by a first pair of walls which are in opposite to each other, said insulating members are formed by a second pair of walls which are in opposite to each other and are interposed between said first pair of walls as said electrodes so as to define a hollow tube with a rectangular cross sectional configuration;
   said first and second supporting members are disposed at the respective ends, of said hollow tube; and
   said first and second light guiding members have a first and a second optically transparent disposed adjacent to said first and second supporting members, so as to define said second and third passages, respectively.

* * * * *